(12) United States Patent
Patterson et al.

(10) Patent No.: US 10,255,337 B2
(45) Date of Patent: Apr. 9, 2019

(54) HEALTH CARE INFORMATION SYSTEM AND METHOD FOR TRANSFORMING HEALTH CARE DATA WITH A TRANSFORMATION PIPELINE

(71) Applicant: Change Healthcare Holdings, LLC, Nashville, TN (US)

(72) Inventors: Chris Patterson, Oakland, CA (US); Arien Malec, Oakland, CA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 288 days.

(21) Appl. No.: 14/673,920

(22) Filed: Mar. 31, 2015

(65) Prior Publication Data

US 2016/0292241 A1 Oct. 6, 2016

(51) Int. Cl.
| | | |
|---|---|---|
| *G06F 7/00* | (2006.01) | |
| *G06F 17/00* | (2006.01) | |
| *G06F 17/30* | (2006.01) | |
| *G16H 10/60* | (2018.01) | |
| *G16H 40/20* | (2018.01) | |

(52) U.S. Cl.
CPC ....... *G06F 17/30563* (2013.01); *G16H 10/60* (2018.01); *G16H 40/20* (2018.01)

(58) Field of Classification Search
None
See application file for complete search history.

(56) References Cited

U.S. PATENT DOCUMENTS

| | | | | |
|---|---|---|---|---|
| 2005/0278374 | A1* | 12/2005 | Patrick | G06F 17/30286 |
| 2008/0104615 | A1* | 5/2008 | Nolan | G16H 10/60 |
| | | | | 719/328 |
| 2009/0316780 | A1* | 12/2009 | Tchernatinsky | H04N 19/176 |
| | | | | 375/240.02 |
| 2010/0026682 | A1* | 2/2010 | Plowman | G06T 15/40 |
| | | | | 345/419 |
| 2010/0274573 | A1* | 10/2010 | Feied | G06Q 50/22 |
| | | | | 705/2 |
| 2013/0095864 | A1* | 4/2013 | Marovets | H04W 4/14 |
| | | | | 455/466 |
| 2015/0074129 | A1* | 3/2015 | Friedrich | G06F 17/30289 |
| | | | | 707/756 |

(Continued)

*Primary Examiner* — Binh V Ho
(74) *Attorney, Agent, or Firm* — Alston & Bird LLP

(57) ABSTRACT

A health care information system, method and computer program product are provided to transform health care data in an efficient manner. In the context of a health care information system, the health care information system includes processing circuitry configured to define a transformation pipeline that includes a plurality of ordered transform elements. The processing circuitry is also configured to ingest health care data with the transformation pipeline in order to transform the health care data. The processing circuitry is further configured to track propagation of data representative of or associated with the health care data through the transformation pipeline. The processing circuitry is configured to track the propagation by identifying one or more completed transform elements that have completed processing of the data and by also identifying one or more ongoing transform elements that have begun processing of the data but for which the processing is incomplete.

20 Claims, 4 Drawing Sheets

(56) References Cited

U.S. PATENT DOCUMENTS

| | | | | |
|---|---|---|---|---|
| 2015/0227681 A1* | 8/2015 | Courchesne | ......... | C12Q 1/6883 |
| | | | | 506/9 |
| 2015/0372807 A1* | 12/2015 | Khoyi | ..................... | H04L 63/04 |
| | | | | 713/150 |
| 2016/0048655 A1* | 2/2016 | Maitra | ................ | G06F 19/3456 |
| | | | | 705/3 |
| 2016/0378919 A1* | 12/2016 | McNutt | .................. | G06Q 50/24 |
| | | | | 705/3 |

* cited by examiner

HEALTH CARE INFORMATION SYSTEM AND METHOD FOR TRANSFORMING HEALTH CARE DATA WITH A TRANSFORMATION PIPELINE

TECHNOLOGICAL FIELD

An example embodiment of the present invention relates generally to a health care information system and method and, more particularly, to a health care information system, method and computer program product for transforming health care data with a transformation pipeline.

BACKGROUND

Health care information systems receive, process and output a wide variety of health care data. For example, health care information systems may work with different types of health care data including data relating to the medical history of a patient, clinical data, patient data defining the birthdate, address and other personal information of a patient, data relating to the result of various tests or procedures or the like. The health care data may be received by health care information systems from a wide variety of sources and the health care information systems may, in turn, provide output to a wide variety of recipients. For example, health care information systems may receive and provide data to various health care providers, patients, laboratories, pharmaceutical companies or the like.

The health care data may be received in a variety of different formats. For example, health care data may have different formats depending upon the source of the health care data or the type of health care data. In order to perform analytics upon the health care data and/or to display the health care data in a manner that is readily understood by an end user, the health care data may be transformed, such as by being normalized, prior to the performance of analytics or projections based upon the health care data and prior to the display of the health care data for end users. By transforming the health care data including normalizing the health care data, the variations in the health care data brought about by different formats and/or different sources may be reduced or eliminated and the health care data may be represented in a manner that is more meaningful for the end user.

The transformations applied to health care data may vary depending upon a variety of factors including the source of the health care data, the format of the health care data, the type of health care data, the purpose of the health care data or the like. By way of example, however, the transformation of health care data may include parsing the health care data received from various sources, extracting health care facts and metadata, extracting features from unstructured data and from additional features, normalizing the data, recoding the data to a different format, etc. Once transformed, the transformed data may be subject to a variety of data analytics and/or a variety of projections of the transformed data may be generated in order to provide additional information to an end user.

Over the course of time, the transformations to be applied to the health care data may change or the health care data itself may change. In these instances, the health care data may again be transformed to ensure that the analytics and projections of the data are current. However, the repeated transformation of the health care data as the health care data changes and/or as the transformations change may create inefficiencies with respect to the processing of the health care data and undesirably consume processing resources of the health care information system.

As noted above, the health care data received from different sources may be formatted in different manners. As such, a health care information system may include different transform elements in order to transform the health care data received from different sources with the transform elements configured to perform the same functions but to act on differently formatted data. For example, a first transform element may be configured to transform the health care data received from a first source, while a second transform element may be configured to transform the health care data received from the second source. The transformation that is performed by the first and second transform elements may be the same, but the first and second transform elements may need to be separately developed and maintained in order to accomplish the same type of transformation for health care data received from the different sources. This redundancy in the transform elements may also lead to inefficiencies in the development and maintenance of the transform elements of a health care information system.

BRIEF SUMMARY

A health care information system, method and computer program product are provided in accordance with an example embodiment in order to transform health care data in an efficient manner. In this regard, the health care information system, method and computer program product of an example embodiment track the propagation of data through a transformation pipeline consisting of a plurality of transform elements such that only those transform elements that are ongoing need be repeated following a transformation failure and not the transform elements that have been completed prior to the transformation failure, thereby increasing the efficiency with which the health care data is transformed. The health care information system, method and computer program product of an example embodiment also permit metadata to be associated with the transform data with the metadata identifying the transform elements of the transformation pipeline that produced the transformed data, thereby permitting the transformed data that should be again subjected to transformation to be readily identified in response to a change in a transform element, such as a change in the version of a transform element. Further, the health care information system, method and computer program product of an example embodiment provide for one or more of the transform elements of the transformation pipeline to be configured to transform health care data that has a neutral health care data format, as opposed to a system-specific data format, thereby permitting at least some of the transform elements to be utilized in conjunction with the transformation of health care data from different sources.

In an example embodiment, a health care information system is provided that is configured to transform health care data. The health care information system includes processing circuitry configured to define a transformation pipeline that includes a plurality of ordered transform elements, such as by determining the plurality of ordered transform elements to be applied to the health care data based at least partially upon the source of the health care data. The processing circuitry of this example embodiment is also configured to ingest health care data with the transformation pipeline in order to transform the health care data. The processing circuitry of this example embodiment is further configured to track propagation of data representative of or associated with the health care data through the transformation pipeline. The processing circuitry of this example embodiment is configured to track the propagation by identifying one or more completed transform elements that have completed processing of the data representative of or associated with the health care data and by also identifying one or more ongoing transform elements that have begun processing of the data representative of or associated with the health care data but for which the processing is incomplete.

The processing circuitry of an example embodiment is additionally configured to receive notification of a transformation failure and to determine the one or more ongoing transform elements when the transformation failure occurred. In this example embodiment, the processing circuitry is also configured to recommence transformation of the health care data with the one or more ongoing transform elements when the transformation failure occurred without repeating the processing provided by the one or more completed transform elements.

The transformation pipeline produces transformed data. The processing circuitry of an example embodiment is also configured to associate metadata with the transformed data. The metadata includes a transformation graph that provides an identification of each of the transform elements of the transformation pipeline that produced the transformed data associated with the metadata. The metadata may include an identification of a version of each of the transform elements of the transformation pipeline and/or an identification of a version of the health care data ingested with the transformation pipeline to produce the transformed data associated with the metadata.

The transform elements of an example embodiment include one or more system-specific transform elements configured to transform health care data that has a respective data format to a neutral health care data format. The transform elements of this example embodiment also include one or more system-neutral transform elements configured to transform health care data that has the neutral health care data format.

In another embodiment, a method for transforming health care data is provided that includes defining a transformation pipeline that includes a plurality of ordered transform elements, such as by determining the plurality of ordered transform elements to be applied to the health care data based at least partially upon a source of the health care data. The method of this example embodiment also includes ingesting health care data with the transformation pipeline in order to transform the health care data. The method of this example embodiment further includes tracking propagation of data representative of or associated with the health care data through the transformation pipeline. The method of this example embodiment tracks the propagation by identifying the one or more completed transform elements that have completed processing of the data representative of or associated with the health care data and also identifying the one or more ongoing transform elements that have begun processing of the data representative of or associated with the health care data but for which the processing is incomplete.

The method of an example embodiment also includes receiving notification of a transformation failure and determining the one or more ongoing transform elements when the transformation failure occurred. The method of this example embodiment further includes recommencing transformation of the health care data with the one or more ongoing transform elements when the transformation failure occurred without repeating the processing provided by the one or more completed transform elements.

The transformation pipeline produces transformed data. In an example embodiment, the method includes associating metadata with the transform data. The metadata includes a transformation graph that provides an identification of each of the transform elements of the transformation pipeline that produces the transformed data associated with the metadata. The metadata of an example embodiment includes an identification of a version of each of the transform elements of the transformation pipeline and/or a version of the health care data ingested with the transformation pipeline to produce the transformed data associated with the metadata. The transform elements of an example embodiment include one or more system-specific transform elements configured to transform health care data that has a respective data format to a neutral health care data format. The transform elements of this example embodiment also include one or more system-neutral transform elements configured to transform health care data that has the neutral health care data format.

In a further example embodiment, a computer program product is provided for transforming health care data. The computer program product includes at least one non-transitory computer-readable storage medium having computer-executable program code portions stored therein with the computer-executable program code portions including program code instructions for defining a transformation pipeline including a plurality of ordered transform elements. The computer-executable program code portions of this example embodiment also include program code instructions for ingesting health care data with the transformation pipeline in order to transform the health care data. The computer-executable program code portions further include program code instructions for tracking propagation of data representative of or associated with the health care data through the transformation pipeline. In this example embodiment, the program code instructions for tracking the propagation include program code instructions for identifying one or more completed transform elements that have completed processing of the data representative of or associated with the health care data and program code instructions for identifying one or more ongoing transform elements that have begun processing of the data representative of or associated with the health care data but for which the processing is incomplete.

The computer-executable program code portions of an example embodiment also include program code instructions for receiving notification of a transformation failure and determining the one or more ongoing transform elements when the transformation failure occurred. The computer-executable program code portions of this example embodiment also include program code instructions for recommencing transformation of the health care data with the one or more ongoing transform elements when the transformation failure occurred without repeating the processing provided by the one or more completed transform elements.

The transformation pipeline produces transformed data. The computer-executable program code portions of an example embodiment further include program code instructions for associating metadata with the transformed data. The metadata includes the transformation graph that provides an identification of each of the transform elements of the transformation pipeline that produces the transformed data associated with the metadata. The metadata of an example embodiment includes an identification of a version of each of the transform elements of the transformation pipeline and/or a version of the health care data ingested with the transformation pipeline to produce the transformed data associated with the metadata. In an example embodiment, the transform elements include one or more system-specific transform elements configured to transform health care data that has a respective data format to a neutral health care data format. In this example embodiment, the transform elements also include one or more system-neutral transform elements configured to transform health care data that has the neutral health care data format.

BRIEF DESCRIPTION OF THE DRAWINGS

Figure 1:
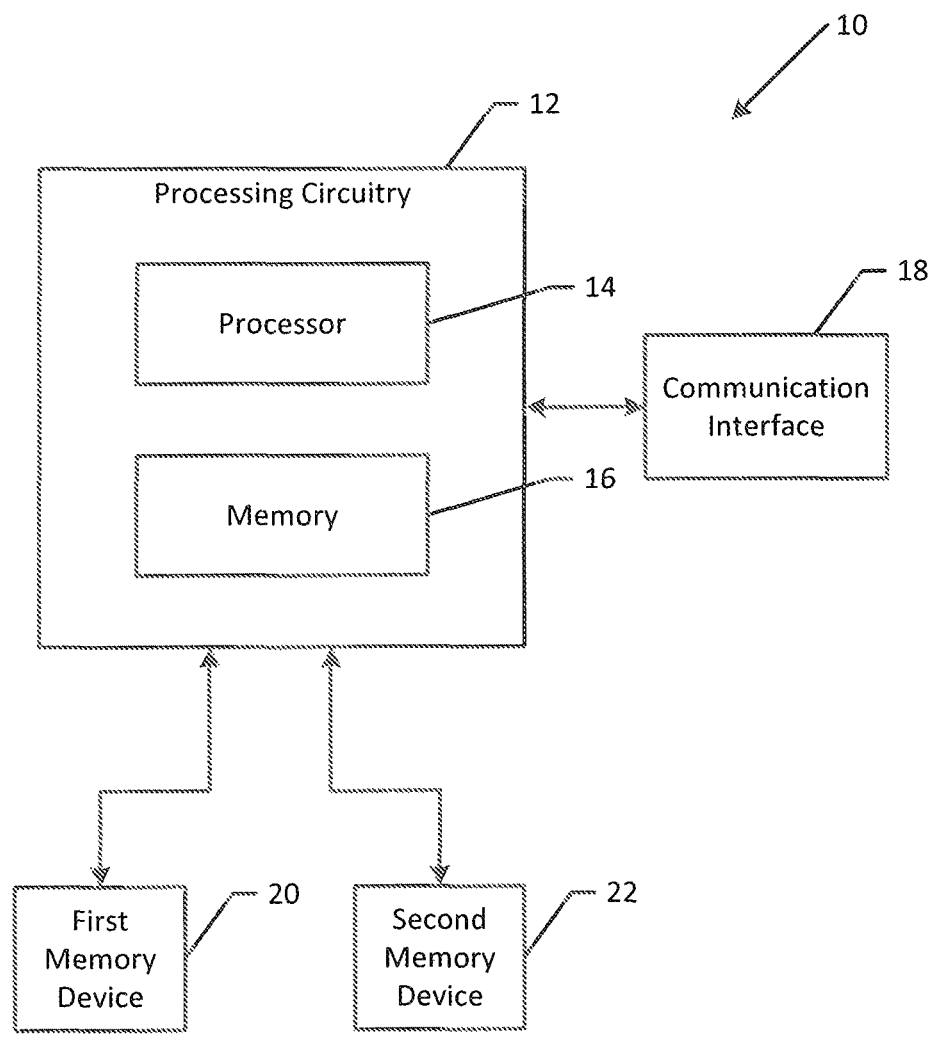
Figure 2:
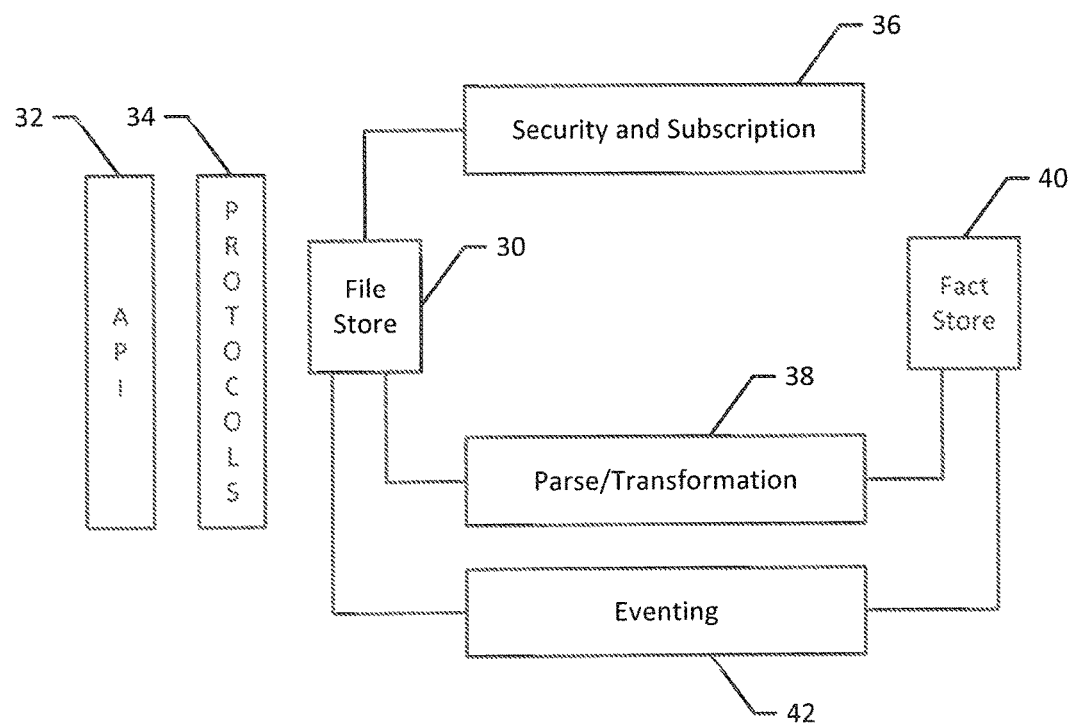
Figure 3:
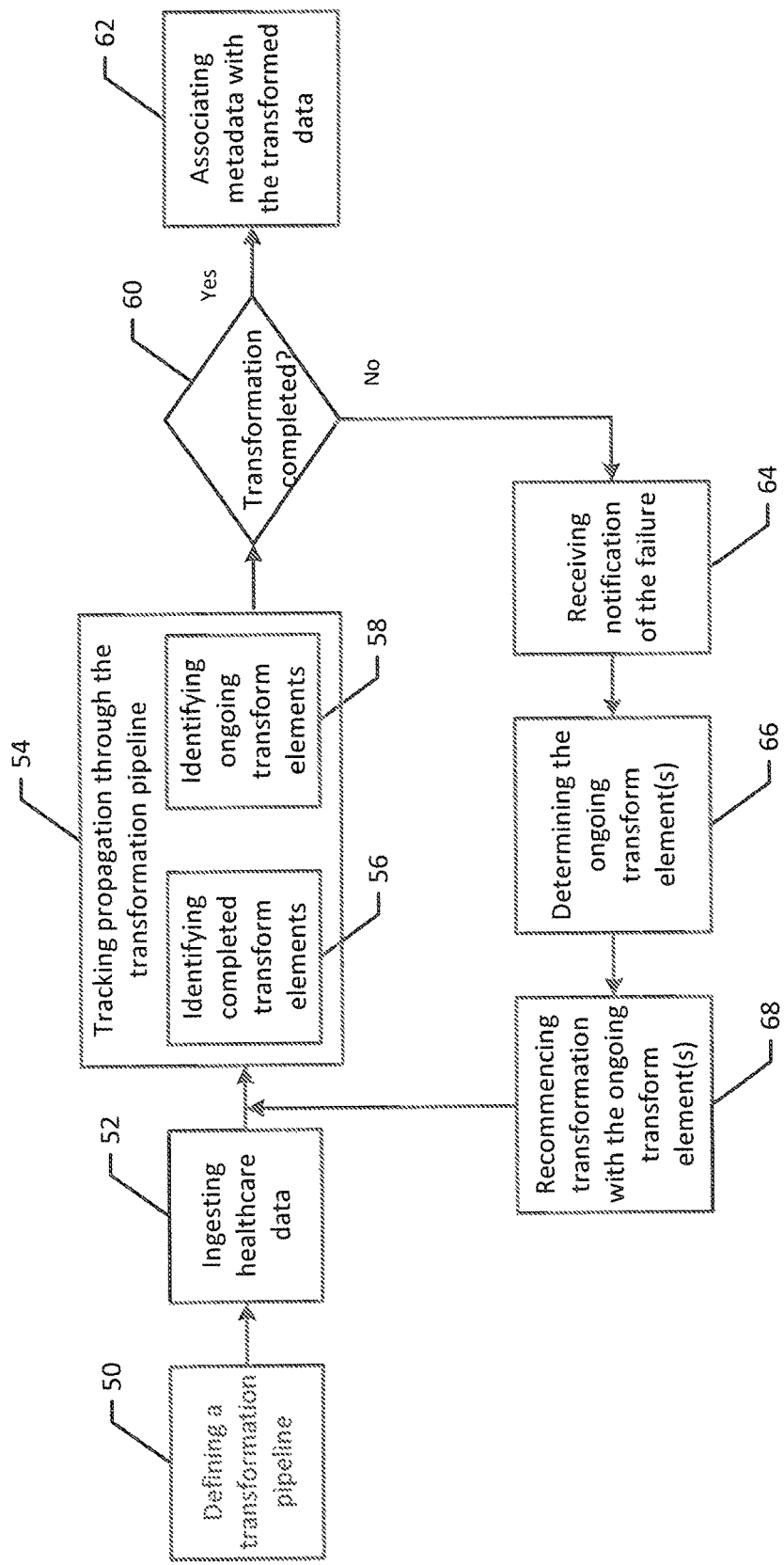
Figure 4:
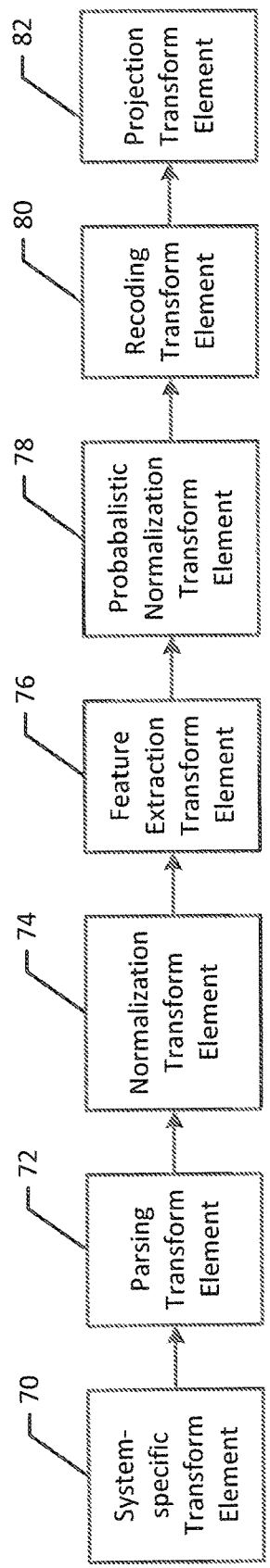

Having thus described certain example embodiments of the present disclosure in general terms, reference will hereinafter be made to the accompanying drawings, which are not necessarily drawn to scale, and wherein:

FIG. 1 is a block diagram of a health care information system that may be specifically configured in accordance with an example embodiment of the present invention;

FIG. 2 is a more detailed block diagram of a health care information system that may be specifically configured in accordance with an example embodiment of the present invention;

FIG. 3 is a flowchart of the operations performed, such as by the health care information system of FIG. 1 or 2, for transforming health care data in accordance with an example embodiment of the present invention; and FIG. 4 is a block diagram illustrating a plurality of transform elements that may be ordered to define a transformation pipeline in accordance with an example embodiment of the present invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received and/or stored in accordance with embodiments of the present invention. Thus, use of any such terms should not be taken to limit the spirit and scope of embodiments of the present invention.

A health care information system, method and computer program product are provided in accordance with an example embodiment in order to efficiently and accurately transform health care data. In an example embodiment, the health care information system, method and computer program product are configured to transform health care data that is received from a wide variety of sources in different respective formats to transformed data that permits analytics and other projections of the transformed data to be generated in an accurate and consistent manner. The health care information system, method and computer program product of an example embodiment provide for the efficient transformation of health care data even in an instance in which a transformation failure occurs by permitting the transformation of the health care data to be recommenced following a transformation failure such that only those transform elements that were ongoing when the transformation failure occurred are repeated.

The health care information system, method and computer program product of an example embodiment may associate metadata with the transformed data in order facilitate further transformation of the health care data if the health care data and/or the transformation pipeline is updated or otherwise changes. Further, the health care information system, method and computer program product of an example embodiment may transform health care data having a respective data format, such as a data format specific to a respective source, to a neutral health care data format such that other system-neutral transform elements may thereafter transform the health care data that has the neutral health care data format. As such, the health care information system, method and computer program product of this example embodiment may be more efficiently constructed and maintained by utilizing the system-neutral transform elements that are more universally applicable regardless of the data format of the health care data ingested by the transformation pipeline.

The health care information system may be embodied by a variety of different computer systems that are configured to receive, process and output health care information. Regardless of the type of computer system that embodies the health care information system, the health care information system includes or is associated and in communication with processing circuitry 12 as shown in FIG. 1 that is configurable to perform functions in accordance with one or more example embodiments disclosed herein. In this regard, the processing circuitry may be configured to perform and/or control performance of one or more functionalities of the health care information system in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 12 includes a processor 14 and, in some embodiments, such as that illustrated in FIG. 1, further includes memory 16. The processing circuitry may also be in communication with or otherwise control a communication interface 18 for communicating with other computing systems. As such, the processing circuitry may be embodied as a circuit chip (e.g., an integrated circuit chip) configured (e.g., with hardware, software or a combination of hardware and software) to perform operations described herein.

The processor 14 may be embodied in a number of different ways. For example, the processor may be embodied as various processing means such as one or more of a central processing unit, a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device as described herein. The plurality of processors may be embodied on a single computing device or distributed across a plurality of computing devices collectively configured to function as the computing device. In some example embodiments, the processor may be configured to execute instructions stored in the memory 16 or otherwise accessible to the processor. As such, whether configured by hardware or by a combination of hardware and software, the processor may represent an entity (e.g., physically embodied in circuitry—in the form of processing circuitry 12) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

The processing circuitry 12 may also include memory 16 as shown in FIG. 1. In some example embodiments, the memory may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The memory may be configured to store information, data, applications, instructions and/or the like for enabling the computing device to carry out various functions in accordance with one or more example embodiments. For example, the memory may be configured to buffer input data for processing by the processor 14. Additionally or alternatively, the memory may be configured to store instructions for execution by the processor. Among the contents of the memory, applications may be stored for execution by the processor in order to carry out the functionality associated with each respective application. In some cases, the memory may be in communication with the processor via a bus or buses for passing information among components of the health care information system 10.

As noted above, the health care information system 10 of the embodiment of FIG. 1 also includes a communication interface 18. The communication interface of an example embodiment may be in communication with one or more sources of health care data so as to receive the health care data therefrom, which may then be transformed as described herein. The communication interface may be any means such as a device or circuitry embodied in either hardware or a combination of hardware and software that is configured to receive and/or transmit messages from sources to subscribers. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication.

The communication interface 18 may be configured to directly and/or indirectly communicate with the sources of health care data in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G, 3G, 4G or Long Term Evolution (LTE) communication techniques, local area network (LAN), wireless LAN (WLAN) techniques or the like. In accordance with various ones of these techniques, the communication interface can be coupled to and configured to communicate across one or more networks. The network(s) can comprise any of a number of different combinations of one or more different types of networks, including data and/or voice networks. For example, the network(s) can include one or more data networks, such as a LAN, a metropolitan area network (MAN), and/or a wide area network (WAN) (e.g., Internet), and include one or more voice networks, such as a public-switched telephone network (PSTN).

As shown in FIG. 1, the health care information system 10 may also include a plurality of additional memory devices in communication with the processing circuitry 12. For example, the health care information system may include first and second memory devices 20, 22 as depicted in FIG. 1, although the health care information system may include additional memory devices in other example embodiments. The plurality of memory devices, such as the first and second memory devices, may include different types of memory devices depending upon the type of information to be stored by the memory device and the access requirements for the type of information. As described below in conjunction with the embodiment of FIG. 2, for example, the first memory device may serve as a file store and, as such, may be embodied by a type of memory configured to store large amounts of information in an efficient manner, such as a binary large object (BLOB) storage, and the second memory device may be embodied by a key value store or other type of storage configured to efficiently store and access tabular information.

Referring now to FIG. 2, the health care information system 10 in accordance with an example embodiment is depicted. The health care information system of the embodiment of FIG. 2 receives data via an application programming interface (API) 32 that may be embodied, for example, by the communication interface 18, the processing circuitry 12, such as the processor 14, or the like. Prior to storing the data elements that are received via the API within the file store 30, the health care information system may subject the data to one or more protocols 34 in order to obtain a normalized set of facts. The protocols may also be defined and/or implemented by the communication interface, the processing circuitry, such as the processor, or the like. In this regard, the protocols may identify the parse and/or transformation logic to be applied to the data in order to obtain a normalized set of facts. The protocols may be based upon the type of data, the data source and/or the eventual recipient of the data. In this regard, some protocols may apply to all data types. For example, the same protocol may apply to the definition of a person, the definition of an address, etc. regardless of the type of data within which the person or address is defined. In contrast, other protocols are specific to a particular data type or a particular source or intended recipient of the data.

The health care information system 10 of this example embodiment also includes a file store 30 for storing the data received via the API 32 once the corresponding protocols 34 have identified the parse and transformation logic to be associated with the data element. The file store may be embodied by the first memory device 20 and, in one embodiment, is embodied by a type of memory device that efficiently stores large amounts of information, such as BLOB storage. In an example embodiment, the data is hashed, such as by the processing circuitry 12, e.g., the processor 14, prior to storage by the file store.

The data received by the health care information system 10 may be encrypted or otherwise secured, such as with an asymmetric encryption technique utilizing public and private keys. In order to enhance the security associated with the data, the keys may be rotated over the course of time. As such, the health care information system may include security and subscription logic 36, such as may be embodied by the processing circuitry 12, such as the processor 14. As described above, the health care information system also includes parse and transformation logic 38, such as may also be embodied by the processing circuitry, such as the processor. The manner in which a data element is to be processed by the parse and transformation logic is described below and may be defined by a protocol based upon the data type and/or the data source and intended recipient. The parse and transformation logic is configured to normalize the data element so as to produce a normalized set of facts. As described below, the parse and transformation logic may also generate projections of the data. The normalized set of facts and projections may be stored, for example, by the fact store 40. In this regard, the fact store may be embodied by a different memory device than the memory device that embodies the file store 30. In this regard, the fact store may be embodied by the second memory device 22 which may be embodied by a type of memory device that efficiently creates and accesses tables, such as a key value store. In addition to the set of normalized facts and projections generated by the parse and transformation logic, the fact store may store a pointer to the location within the file store at which the underlying data elements are stored.

As described below, the health care information system 10 of an example embodiment is also configured to create and publish events based upon one or a combination of the data elements. As such, the health care information system of this example embodiment includes eventing logic 42, such as may be embodied by the processing circuitry 12, such as the processor 14, in order to detect predefined types of events and to publish notifications of such events to subscriber(s) of the respective type of event.

The operations performed by a health care information system 10 and method in accordance with an example embodiment are depicted in FIG. 3. As shown in block 50, the health care information system includes means, such as the processing circuitry 12, such as the processor 14, the protocols 34, the parse and transformation logic 38 or the like, for defining a transformation pipeline that includes a plurality of ordered transform elements. Each transform element of the transformation pipeline is configured to perform a respective function such that by ordering a plurality of transform elements, such as in a serial fashion as shown in FIG. 4, the resulting transformation pipeline is configured to transform the health care data that is ingested in the desired manner.

The particular types of transform elements and the order in which the transform elements are sequenced depends upon various factors including the source of the health care data, the type of health care data, the analytics to be performed upon the health care data, the projections to be created based upon the health care data, etc. Thus, the health care information system 10 of an example embodiment includes means, such as the processing circuitry 12, such as the processor 12, the protocols 34, the parse and transformation logic 38 or the like, for determining the plurality of ordered transform elements to be applied to the health care data based at least partially upon the source of the health care data. In this regard, the processing circuitry may define the transform elements and the order of those transform elements to be assembled to form the transformation pipeline in order to transform the health care data from the form in which the health care data is received to a form that is desirable for further processing, review or storage, such as to a form suitable for the performance of analytics or projections and/or to a form suitable for display to an end user.

By way of example, but not of limitation, FIG. 4 depicts a transformation pipeline that includes a plurality of ordered transform elements. Each transform element is configured to perform a respective function with respect to the data representative of or associated with the health care data that is ingested by the transformation pipeline. In the example depicted in FIG. 4, the transformation pipeline includes a parsing transform element 72. The parsing transform element separates the incoming data into different portions, such as into the different fields or segments. The transformation pipeline of the example of FIG. 4 also includes a normalization transform element 74 in order to normalize the data. The data may be normalized in various manners. For example, the normalization transform element may be configured to perform terminology normalization and/or identity normalization. Based upon the normalization, data representative of the same type of information, such as a name, address, diagnostic code, etc., may be represented in the same manner regardless of the manner in which the information was represented upon receipt by the normalization element. By way of example, a normalization transform element may be configured to normalize dates to an international organization for standardization (ISO) format and/or to provide for identity normalization, e.g., the normalization of names to a constant format.

In the example of FIG. 4, the transformation pipeline also includes a feature extraction transform element 76 and/or a probabilistic normalization transform element 78. The feature extraction transform element may be configured to extract various types of features from the data, such as based upon natural language processing of the data. By way of example, the feature extraction transform element may extract the metadata, such as identity and/or transactional identifiers, from the other, underlying data. The probabilistic normalization transform element may be configured to make various inferences depending upon the data received thereby. For example, one example of a probabilistic normalization transform element is configured to infer from the existence of multiple ICD9 codes and/or medication terms, the existence or non-existence of a health issue. The transformation pipeline of the example embodiment of FIG. 4 also includes a recoding transform element 80. The recoding transform element may be configured to transform the data from one format to another format, such as from an ICD9 format to SNOMED-CT format. Although an example of a transformation pipeline is depicted in FIG. 4 and has been described above, the transformation pipeline of FIG. 4 is merely an example and the health care information system and method of an example embodiment may be configured to define a wide variety of other transformation pipelines including different transform elements and/or differently ordered transform elements.

In this regard and by way of further example, a transformation pipeline of an example embodiment may be configured to ingest health care data in the form of a document that includes an observation provided by a laboratory which indicates the glucose level of a patient. The document, including the observation, may be in an HL7 observation result (ORU) format. Upon receipt, the transformation pipeline of this example embodiment may be configured to extract or convert the observation into a neutral format for the respective type of data. The transformation pipeline may then calculate an average glucose reading over the past 90 days, including the most recently received glucose reading that has been converted to a neutral format. The derived fact, namely, the average glucose reading, is then stored and is also compared to a threshold relating to being at risk for diabetes. In an instance in which the average glucose reading satisfies, such as by exceeding, the threshold, an alert may be triggered and transmitted to the patient's physician. The calculation of the average glucose reading may also cause the analytics to be updated that define the geographic distribution of patients that have been determined to be at risk for diabetes and/or the percentage of a practice's patient population to have been determined to be at risk for diabetes.

As another example of a transformation pipeline, the web-enabled glucose meter of a patient who is at risk for diabetes may report the glucose readings as taken multiple times a day. The data delivered by the glucose meter is in a data format that is proprietary to the manufacturer. Upon receipt of the data from the glucose meter, the data may be stored in its original format. The data that is ingested may also be subjected to a real-time transformation to convert its format to a neutral format for a glucose reading. Throughout the transformation pipeline, the source of the data is retained in association with the data (and in association with the data that is stored) to insure that the provenance of the data is available to the physician. Based upon the source of the data, the transformation pipeline of this example embodiment may determine that the newly ingested data should only be averaged with other data of the same type from the same source and should not be averaged with other measurements of the patient's glucose level from other sources since the data measured by the various sources may have different degrees of accuracy and consistency.

The transformed data generated by the transformation pipeline may be stored, such as by the second memory device 22, e.g., the fact store 40. Additionally or alternatively, the transformed data may be displayed for review by an end user. Still further, the transformed data may be further processed. For example, the transformation pipeline may optionally include a projection transform element 82 (or the projection transform element may be positioned downstream of the transformation pipeline). The projection transform element is configured to create projections of the transformed data. Various projections of the data may be generated including graphical or tabular representations of the transformed data, such as by assembling the current problem list for a patient or creating the tabulation of medication values for a set of patients. The resulting projections may be displayed to an end user. In addition or alternatively, the transformed data following transformation via the transformation pipeline may be subjected to various data analytics with the results of the data analytic being stored, such as by the second memory device, e.g., the fact store, and/or displayed for the end user.

As noted above, the health care data received by the health care information system 10 may be any of a variety of different types of health care data and may be provided by any of a variety of sources. As such, the health care data that is received by the health care information system may be differently formatted depending upon the type of health care data, the source of the health care data or the like. In an example embodiment, at least some of the transform elements are system-specific transform elements that are configured to transform health care data that has a respective data format to a neutral health care data format. Thus, health care data that is received in a particular data format, such as due to the respective type of health care data and/or the respective source of the health care data, is transformed by a system-specific transform element that is configured to process the particular data format in which the health care data is received to the neutral health care data format. In this example embodiment, the transform elements also include one or more system-neutral transform elements configured to transform health care data that has a neutral health care data format. As such, once the system-specific transform element has transformed health care data having a particular data format to the neutral health care data format, the system-neutral transform elements are configured to process the health care data in the neutral health care data format.

With respect to the example of FIG. 4, the system-specific transform element 70 is configured to transform the health care data received by the transformation pipeline in a particular fox mat to a neutral health care data format. The other transform elements downstream of the system-specific transform element are examples of system-neutral transform elements that are configured to process the health care data in the neutral health care data format. By transforming health care data having a respective data format to a neutral health care data format, the system-neutral transform elements may be utilized in a wide variety of transformation pipelines regardless of the data format in which the health care data is originally presented to the transformation pipeline since the health care data in a respective data format will be converted to a neutral health care data format prior to processing by the system-neutral transform elements. As such, the creation and maintenance of the transform elements, such as the system-neutral transform elements, is made more efficient by the utilization of the system-neutral transform elements in a plurality of transformation pipelines.

At least some of the transform elements, such as the system-neutral transform elements, may be defined, e.g., written or coded, in a manner that is decoupled from a specific system architecture and from a system specific language, such as by being written or coded in a health care transformation expression language that is system independent. Thus, at least some of the transform elements, such as the system-neutral transform elements, can be utilized to transform health care data provided by different types of systems, such as a stream processing system, e.g., an Apache Storm system, and a batch computing system, e.g., a Hadoop map/reduce system. By way of example, the system-neutral transform elements of one embodiment may be a Javascript implementation with core transformers which may be reimplemented to work with a variety of systems, such as the C# transformers in one system or Hadoop map/reduce expressions on Azure-hosed Hadoop in another system.

As shown in block 52 of FIG. 3, the health care information system 10 also includes means, such as the processing circuitry 12, such as the processor 14, the communication interface 18 or the like, for ingesting health care data with the transformation pipeline. Once ingested, the health care data is transformed by the ordered transform elements of the transformation pipeline, such as described above.

As shown in block 54 of FIG. 3, the health care information system 10 also includes means, such as the processing circuitry 12, e.g., the processor 14, or the like, for tracking propagation of data representative of or associated with the health care data through the transformation pipeline. In regards to tracking the propagation of data representative of or associated with the health care data through the transformation pipeline, the health care information system, such as the processing circuitry, of an example embodiment is configured to identify one or more completed transform elements that have completed processing of the data representative of or associated with the health care data. See block 56, Additionally, the health care information system, such as the processing circuitry, is configured to also identify the one or more ongoing transform elements that have begun processing of the data representative of or associated with the health care data, but for which the processing is incomplete.

With respect to the example of a transformation pipeline depicted in FIG. 4, in an instance in which the data representative of or associated with the health care data that was ingested by the transformation pipeline has propagated through the system-specific transform element 70, the parsing transform element 72 and the normalization transform element 74 and is being processed by the feature extraction transformation element 76, the health care information system 10, such as the processing circuitry 12, is configured to identify the system-specific transform element, the parsing transform element and the normalization transform element as completed transform elements, while the feature extraction transform element is identified as an ongoing transform element.

Upon completion or termination of the propagation of data through the transformation pipeline, the health care information system 10, such as the processing circuitry 12, e.g., the processor 14, is configured to determine if the transformation of the health care data has been completed, such as by propagating through the entire transformation pipeline, as shown in block 60. In an instance in which the transformation of the health care data is completed, the health care information system of an example embodiment includes means, such as the processing circuitry, e.g., the processor, or the like, for associating metadata with the transformed data that exits the transformation pipeline. See block 62. In an example embodiment, the health care information system, such as the processing circuitry, generates metadata that is associated with the transformed data that includes a transformation graph that provides an identification of each of the transform elements of the transformation pipeline that produced the transformed data associated therewith.

In at least some embodiments, one or more of the transform elements may be provided in different versions, such as version 1.0, version 1.1, version 1.2, version 2.0, etc. In this example embodiment, the transformation pipeline would generally include the most recent or most current version of the respective transform element at the time at which the health care data is being transformed. Consequently, the processing circuitry 12, such as the processor 14, is configured to generate metadata that not only identifies the transform elements that produced the transformed data, but that also identifies the version of each transform element of the transformation pipeline that produced the transformed data. Additionally or alternatively, the health care data that is transformed may similarly have a version associated therewith. As such, in this example embodiment, the metadata that is generated and associated with the transformed data by the processing circuitry, such as the processor, may include an identification of the version of the health care data ingested by the transformation pipeline that produced the transformed data associated with the metadata.

As such, in an instance in which a different version, e.g., a more current version, of the health care data and/or a different version, e.g., a more current version, of a transform element becomes available, the health care information system 10, such as the processing circuitry 12, is configured to determine the transformed data that was generated by a prior version of the health care data or a prior version of a transform element, such as by an analysis of the metadata associated with the transformed data. The transformation of the health care data may then again be performed, albeit by now utilizing the more current version of the transform elements and/or the more current version of the health care data such that the resulting transformed data is correspondingly updated and maintained current. The metadata associated with the transformed data is also updated to reflect the version of the transform elements and the version of the health care data that produced the updated transformed data.

The transformed data and the metadata associated therewith are stored, such as by the second memory 22, the fact store 40, etc. In addition, at least a portion of the transformed data may be presented to an end user, such as by being displayed. In addition or alternatively, the transformed data may be subjected to data analytics and the result of the data analytics may be stored, such as in the second memory, the fact store, etc., and/or displayed to the end user. Additionally or alternatively, the health care information system 10, such as the processing circuitry 12, of an example embodiment is also configured to create projections of the transformed data, such as projections based upon a particular patient, a particular segment of the patient population or the like. The projections based upon the transformed data may also be stored, such as by the second memory, the fact store, etc., and/or displayed to the end user.

In an instance in which the health care information system 10, such as the processing circuitry 12, determines at block 60 that the transformation has not been completed, the health care information system of an example embodiment includes means, such as the processing circuitry, e.g., the processor 14, the communication interface 18 or the like, for receiving notification of a transformation failure. See block 64. A transformation failure may occur for various reasons including inconsistencies or improprieties with respect to the health care data, improper performance by a respective transform element or the like. The health care information system of this example embodiment also includes means, such as the processing circuitry, e.g., the processor, or the like, for determining one or more ongoing transform elements at the time at which the transformation failure occurred. See block 66. In this regard, the processing circuitry, such as the processor, is configured to track the propagation of the data through the transformation pipeline so as to identify the one or more completed transform elements and the one or more ongoing transform elements.

The health care information system 10 of this example embodiment also includes means, such as the processing circuitry 12, e.g., the processor 14, or the like, for recommencing transformation of the health care data beginning with the one or more ongoing transform elements when the transformation failure occurred. See block 68. By recommencing the transformation of the health care data beginning with the one or more ongoing transform elements, processing provided by the one or more completed transform element(s) is not repeated. As such, the health care information system of this example embodiment is configured to recover from the transformation failure in an efficient manner, while ensuring that the health care data is completely transformed by being fully processed by each transform element of the transformation pipeline. By avoiding any repetition in the processing provided by completed transform element(s), the health care information system of this example embodiment recovers from the transformation failure in a manner that avoids repeating processing activities that have already been successfully completed.

As described above, FIG. 3 is a flowchart of a health care information system 10, method and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 16 and executed by processor 14 of the health care information system. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 12 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A health care information system configured to transform health care data, the health care information system comprising processing circuitry configured to:
    define a transformation pipeline comprising a plurality of ordered transform elements;
    ingest health care data with the transformation pipeline in order to transform the health care data;
    track propagation of processed data representative of or associated with the health care data through the transformation pipeline, wherein the processing circuitry is configured to track the propagation by identifying the one or more completed transform elements that have completed processing of the processed data and also identifying the one or more ongoing transform elements that have begun processing of the processed data but for which the processing is incomplete; and
    upon transformation failure that occurs: (1) after having completed processing of the processed data by one or more completed transform elements and also (2) after having commenced, but prior to having completed, processing of the processed data by one or more ongoing transform elements, recommence transformation of the health care data with the one or more ongoing transform elements that had begun, but not yet completed processing when the transformation failure occurred without repeating the processing provided by the one or more completed transform elements,
    wherein the transformation of the health care data is recommenced after transformation failure with the one or more ongoing transform elements such that the health care data is completely transformed by being fully processed by all of the ordered transform elements.

2. A health care information system according to claim 1 wherein the processing circuitry is further configured to:
    receive notification of a transformation failure; and
    determine the one or more ongoing transform elements when the transformation failure occurred.

3. A health care information system according to claim 1 wherein the processing circuitry is configured to define the transformation pipeline by determining the plurality of ordered transform elements to be applied to the health care data based at least partially upon a source of the health care data.

4. A health care information system according to claim 1 wherein the transformation pipeline produces transformed data, wherein the processing circuitry is further configured to associate metadata with the transformed data, and wherein the metadata includes a transformation graph that provides an identification of each of the transform elements of the transformation pipeline that produced the transformed data associated with the metadata.

5. A health care information system according to claim 4 wherein the metadata includes an identification of a version of each of the transform elements of the transformation pipeline.

6. A health care information system according to claim 4 wherein the metadata includes an identification of a version of the health care data ingested with the transformation pipeline to produce the transformed data associated with the metadata.

7. A health care information system according to claim 1 wherein the transform elements comprise one or more system-specific transform elements configured to transform health care data that has a respective data format to a neutral health care data format, and wherein the transform elements comprise one or more system-neutral transform elements configured to transform health care data that has the neutral health care data format.

8. A method for transforming health care data, the method comprising:
    defining a transformation pipeline comprising a plurality of ordered transform elements;
    ingesting health care data with the transformation pipeline in order to transform the health care data;
    tracking propagation of processed data representative of or associated with the health care data through the transformation pipeline, wherein tracking the propagation comprises identifying the one or more completed transform elements that have completed processing of the processed data and also identifying the one or more ongoing transform elements that have begun processing of the processed data but for which the processing is incomplete; and
    upon transformation failure that occurs: (1) after having completed processing of the processed data by one or more completed transform elements and also (2) after having commenced, but prior to having completed, processing of the processed data by one or more ongoing transform elements, recommencing transformation of the health care data with the one or more ongoing transform elements that had begun, but not yet completed processing when the transformation failure occurred without repeating the processing provided by the one or more completed transform elements,
    wherein the transformation of the health care data is recommenced after transformation failure with the one or more ongoing transform elements such that the health care data is completely transformed by being fully processed by all of the ordered transform elements.

9. A method according to claim 8 further comprising:
    receiving notification of a transformation failure; and
    determining the one or more ongoing transform elements when the transformation failure occurred.

10. A method according to claim 8 wherein defining the transformation pipeline comprises determining the plurality of ordered transform elements to be applied to the health care data based at least partially upon a source of the health care data.

11. A method according to claim 8 wherein the transformation pipeline produces transformed data, wherein the method further comprises associating metadata with the transformed data, and wherein the metadata includes a transformation graph that provides an identification of each of the transform elements of the transformation pipeline that produced the transformed data associated with the metadata.

12. A method according to claim 11 wherein the metadata includes an identification of a version of each of the transform elements of the transformation pipeline.

13. A method according to claim 11 wherein the metadata includes an identification of a version of the health care data ingested with the transformation pipeline to produce the transformed data associated with the metadata.

14. A method according to claim 8 wherein the transform elements comprise one or more system-specific transform elements configured to transform health care data that has a respective data format to a neutral health care data format, and wherein the transform elements comprise one or more system-neutral transform elements configured to transform health care data that has the neutral health care data format.

15. A computer program product for transforming health care data, the computer program product comprising at least one non-transitory computer-readable storage medium having computer-executable program code portions stored therein, the computer-executable program code portions comprising program code instructions for:
    defining a transformation pipeline comprising a plurality of ordered transform elements;
    ingesting health care data with the transformation pipeline in order to transform the health care data;
    tracking propagation of processed data representative of or associated with the health care data through the transformation pipeline, wherein the program code instructions for tracking the propagation comprise program code instructions for identifying the one or more completed transform elements that have completed processing of the processed data and program code instructions for identifying the one or more ongoing transform elements that have begun processing of the processed data but for which the processing is incomplete; and
    upon transformation failure that occurs: (1) after having completed processing of the processed data by one or more completed transform elements and also (2) after having commenced, but prior to having completed, processing of the processed data by one or more ongoing transform elements, recommencing transformation of the health care data with the one or more ongoing transform elements that had begun, but not yet completed processing when the transformation failure occurred without repeating the processing provided by the one or more completed transform elements,
    wherein the transformation of the health care data is recommenced after transformation failure with the one or more ongoing transform elements such that the health care data is completely transformed by being fully processed by all of the ordered transform elements.

16. A computer program product according to claim 15 wherein the computer-executable program code portions further comprise program code instructions for:
    receiving notification of a transformation failure; and
    determining the one or more ongoing transform elements when the transformation failure occurred.

17. A computer program product according to claim 15 wherein the transformation pipeline produces transformed data, wherein the computer-executable program code portions further comprise program code instructions for associating metadata with the transformed data, and wherein the metadata includes a transformation graph that provides an identification of each of the transform elements of the transformation pipeline that produced the transformed data associated with the metadata.

18. A computer program product according to claim 17 wherein the metadata includes an identification of a version of each of the transform elements of the transformation pipeline.

19. A computer program product according to claim 17 wherein the metadata includes an identification of a version of the health care data ingested with the transformation pipeline to produce the transformed data associated with the metadata.

20. A computer program product according to claim 15 wherein the transform elements comprise one or more system-specific transform elements configured to transform health care data that has a respective data format to a neutral health care data format, and wherein the transform elements comprise one or more system-neutral transform elements configured to transform health care data that has the neutral health care data format.

* * * * *